(12) United States Patent
Angelos et al.

(10) Patent No.: US 8,364,244 B2
(45) Date of Patent: Jan. 29, 2013

(54) METHODS AND SYSTEMS TO FACILITATE REDUCING BANDING ARTIFACTS IN IMAGES

(75) Inventors: Elisabeth Angelos, Hartland, WI (US); Sandeep Dutta, Waukesha, WI (US); Jianying Li, New Berlin, WI (US); John Howard Londt, Delafield, WI (US); Melissa L. Vass, Milwaukee, WI (US); Xiangyang Tang, Waukesha, WI (US); Darin R. Okerlund, Muskego, WI (US); Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 1063 days.

(21) Appl. No.: 11/286,938

(22) Filed: Nov. 23, 2005
(Under 37 CFR 1.47)

(65) Prior Publication Data
US 2007/0127797 A1    Jun. 7, 2007

(51) Int. Cl.
*A61B 5/05* (2006.01)
(52) U.S. Cl. .......... 600/425; 600/407; 600/428; 378/14; 378/15; 378/21; 378/62; 378/901
(58) Field of Classification Search .................. 600/407, 600/410, 413, 425, 428, 436, 437; 378/14, 378/15, 21, 62, 901
See application file for complete search history.

(56) References Cited

U.S. PATENT DOCUMENTS

| | | | | |
|---|---|---|---|---|
| 5,406,479 | A * | 4/1995 | Harman | 378/7 |
| 5,493,593 | A * | 2/1996 | Muller et al. | 378/19 |
| 6,418,184 | B1 | 7/2002 | Wang et al. | |
| 6,584,165 | B1 | 6/2003 | Wang et al. | |
| 6,639,965 | B1 * | 10/2003 | Hsieh et al. | 378/8 |
| 6,751,283 | B2 | 6/2004 | van de Haar | |
| 6,757,442 | B1 | 6/2004 | Avinash | |
| 7,529,335 | B2 * | 5/2009 | Bruder et al. | 378/15 |
| 2004/0028173 | A1 | 2/2004 | van de Haar | |
| 2006/0198491 | A1 * | 9/2006 | Taguchi | 378/15 |

OTHER PUBLICATIONS

Manzke et al., "Adaptive Temporal Resolution Optimization in Helical Cardiac Cone Beam CT Reconstruction." 2003. Medical Physics, vol. 30, pp. 3072-3080.*

Wun et al.; "Geometric Instability of Ultrafast Computed Tomographic Coronary Calcium Scores Due to Grey Scale Non-Uniformities";SPIE vol. 2168; pp. 54-65.

* cited by examiner

*Primary Examiner* — James Kish
(74) *Attorney, Agent, or Firm* — Armstrong Teasdale LLP

(57) ABSTRACT

Methods and systems for generating computed tomographic (CT) images from image data acquired during different biological cycles are provided. A computer is programmed to receive a plurality of scan data acquired during a gated acquisition window of each of a plurality of biological cycles, blend the scan data acquired during a first of the plurality of biological cycles with the scan data acquired during a second of the plurality of biological cycles, and construct a final image from the blended data.

18 Claims, 5 Drawing Sheets

METHODS AND SYSTEMS TO FACILITATE REDUCING BANDING ARTIFACTS IN IMAGES

BACKGROUND OF THE INVENTION

This invention relates generally to computed tomography (CT) imaging and more particularly, to reducing banding artifacts in CT cardiac reformatted images.

At least some known Multi-slice CT electrocardiogram (EKG)-gated cardiac reconstruction techniques produce a set of images at a given phase of a cardiac cycle. Data from a range of locations is acquired over a series of heartbeats or cardiac cycles. Images from different cardiac cycles are combined to represent the whole heart through image reformation. The inherently discontinuous sampling in time can give rise to gray scale non-uniformities (banding) in reformatted images.

BRIEF DESCRIPTION OF THE INVENTION

In one embodiment, a computer programmed to generate computed tomographic (CT) images from image data acquired during different biological cycles is provided. The computer is programmed to receive a plurality of scan data acquired during a gated acquisition window of each of a plurality of biological cycles, blend the scan data acquired during a first of the plurality of biological cycles with the scan data acquired during a second of the plurality of biological cycles, and construct a final image from the blended data.

In another embodiment, a method of reconstructing images from image data acquired during different biological cycles is provided. The method includes receiving a plurality of scan data acquired during a gated acquisition window of each of a plurality of biological cycles, blending the scan data acquired during a first of the plurality of biological cycles with the scan data acquired during a second of the plurality of biological cycles, and constructing a final image from the blended data.

In yet another embodiment, a computed tomographic (CT) imaging system for reconstructing an image of an object is provided. The imaging system includes a detector array, at least one radiation source, and a computer coupled to the detector array and the radiation source wherein the computer is configured to receive a plurality of scan data acquired during a gated acquisition window of each of a plurality of biological cycles, blend the scan data acquired during a first of the plurality of biological cycles with the scan data acquired during a second of the plurality of biological cycles, and construct a final image from the blended data.

DETAILED DESCRIPTION OF THE INVENTION

Figure 1:
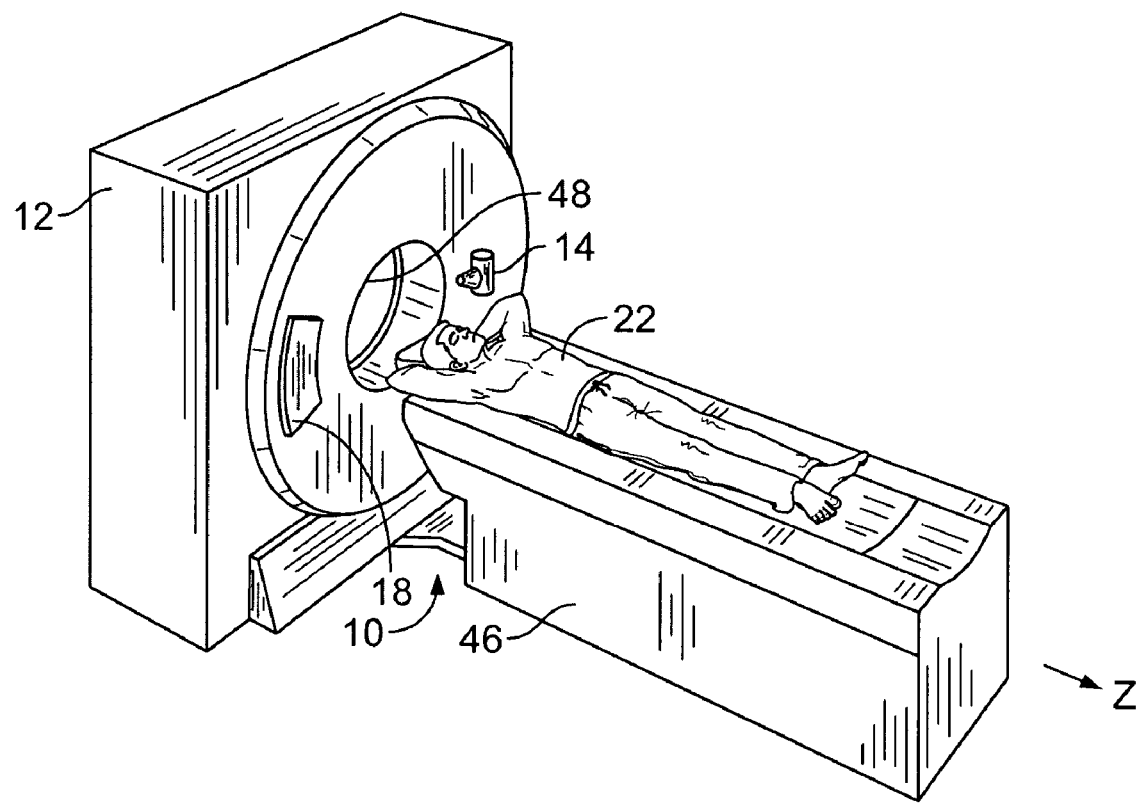
FIG. 1 is a pictorial view of a multi slice volumetric CT imaging system.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image. Additionally, although described in detail in a CT medical setting, it is contemplated that the benefits accrue to all imaging modalities including, for example, ultrasound, Magnetic Resonance Imaging, (MRI), Electron Beam CT (EBCT), Positron Emission Tomography (PET), Single Photon Emission Computed Tomography (SPECT), and in both medical settings and non-medical settings such as an industrial setting or a transportation setting, such as, for example, but not limited to, a baggage scanning CT system for an airport or other transportation center.

Figure 2:
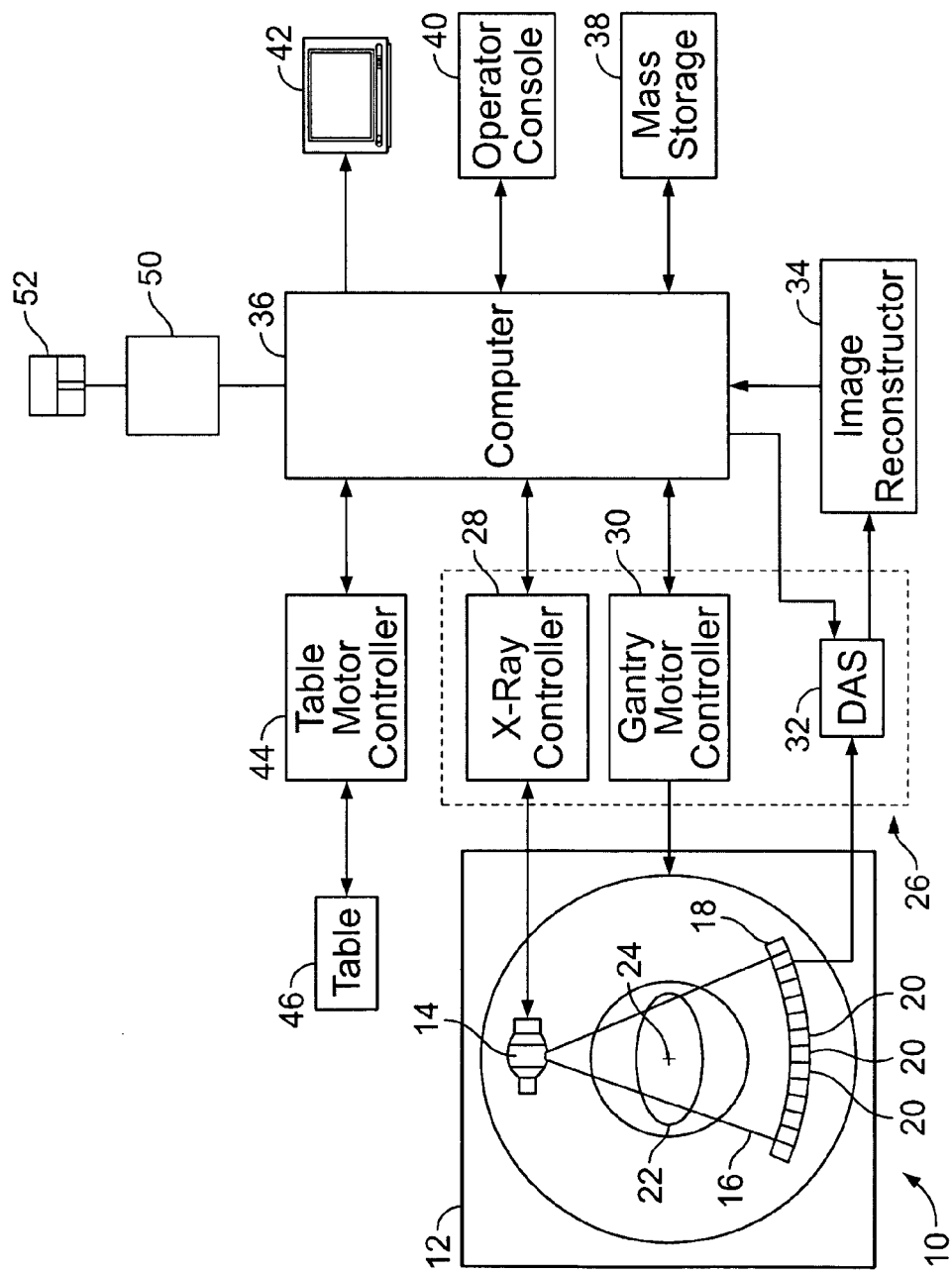
FIG. 2 is a block schematic diagram of the multi slice volumetric CT imaging system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated display system 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Figure 3:
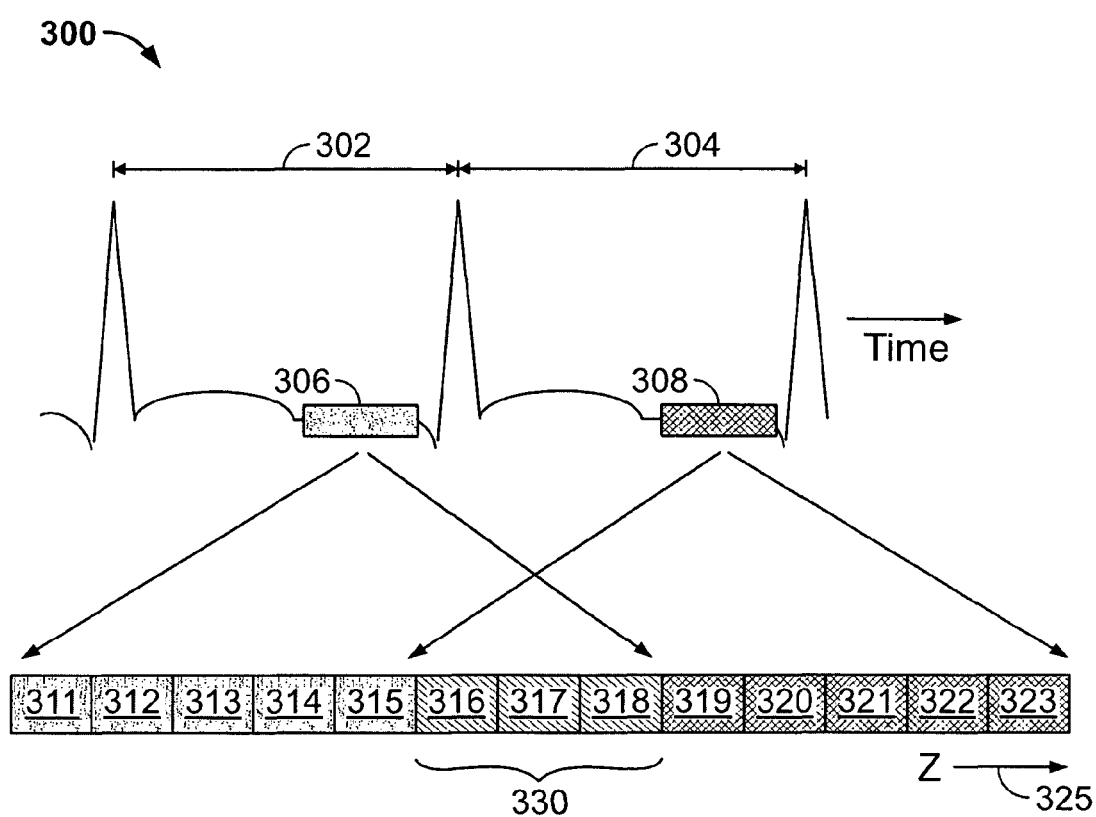
FIG. 3 is a schematic diagram of two exemplary gated cardiac cycles, associated gated acquisition windows, and a plurality of imaging locations along a z axis that are associated with the gated acquisition window.

FIG. 3 is a schematic diagram 300 of two exemplary gated cardiac cycles 302 and 304, associated gated acquisition windows 306 and 308, and a plurality of imaging locations 311-323 along a z axis 325 that are associated with gated acquisition windows 306 and 308. Image locations 311 through 318 include image data acquired during gated acquisition window 306 of cardiac cycle 302. Image locations 316 through 323 include image data acquired during gated acquisition window 308 of cardiac cycle 304. Image locations 316 through 318 include image data acquired during gated acquisition windows 306 and 308. Images from locations 316 through 318 may be reconstructed from data acquired during cardiac cycle 302 and/or cardiac cycle 304.

In the exemplary embodiment, redundant data from multiple heartbeats is used soften the transition between images acquired in different cardiac cycles. Although, such a method does not change temporal resolution as defined by the fraction of the cardiac cycle used for reconstruction, it may cause blurring due to cycle-to-cycle variation in cardiac motion. However, the method does not have the potential loss in resolution associated with methods based on spatial filters.

In the exemplary embodiment, a cardiac scan is a low pitch acquisition that is retrospectively gated by using data from only a portion of each cardiac cycle. To acquire sufficient data for the necessary slice coverage, data is acquired over multiple heartbeats, with each cardiac cycle providing data for several slices. In the exemplary embodiment, each gated acquisition window 306 and 308 include data for eight images. In an alternative embodiment, each gated acquisition window 306 and 308 include data for other than eight images. Banding artifacts occur when the data from one cardiac cycle does not match the data from the next.

In the exemplary embodiment, the helical pitch is set so there is some overlap in the slices that can be reconstructed from each heart beat. Gated acquisition window 306 from cardiac cycle 302 includes data for image locations 311 through 318, and gated acquisition window 308 from cardiac cycle 304 includes data for images locations 316 through 323. Accordingly, there are two different data sets for image locations 316 though 318. In this "transition" region 330, data from one or both of gated acquisition windows 306 and 308 is used to reconstruct an image.

Figure 4:
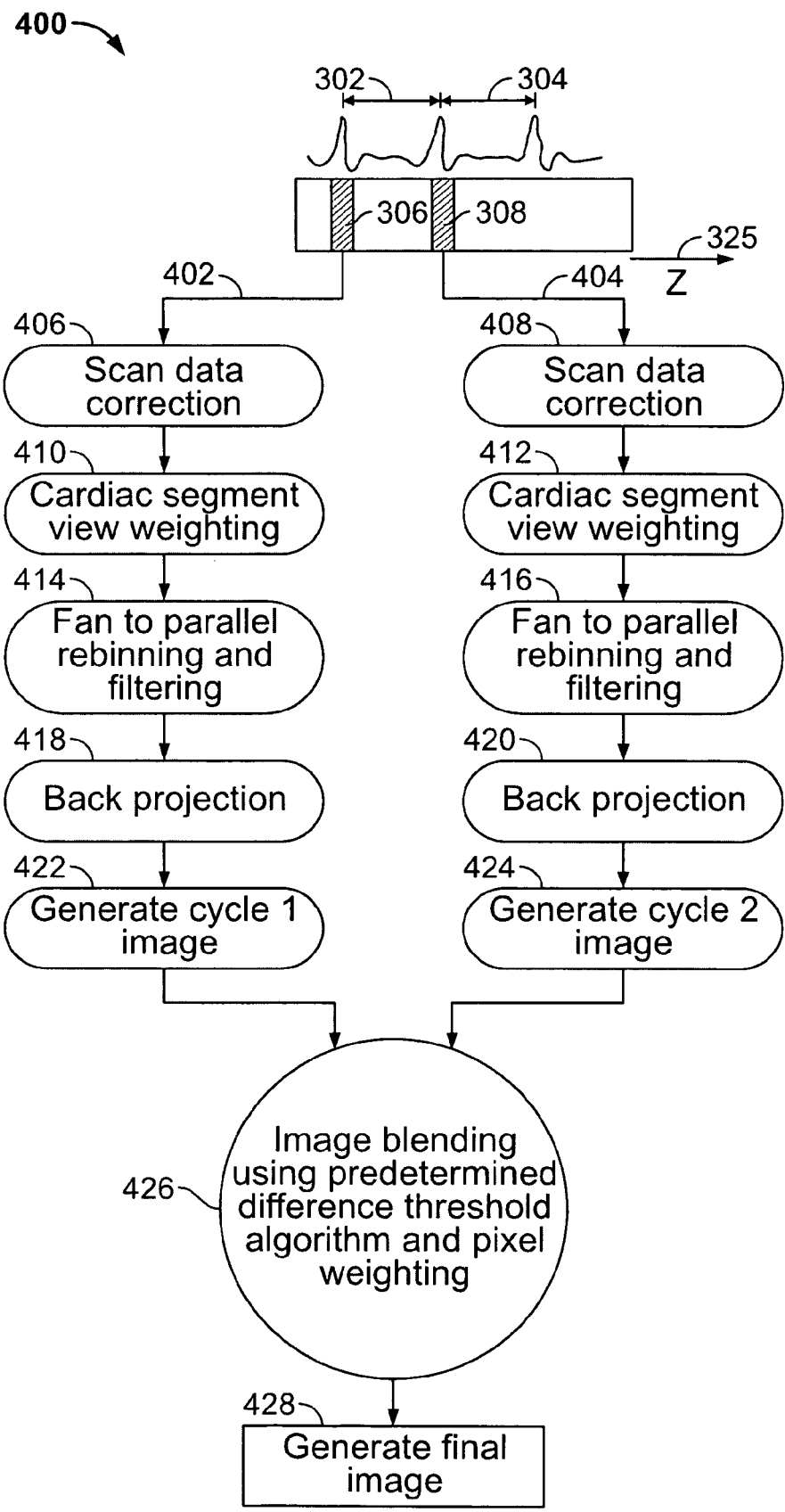
FIG. 4 is a flow chart of an exemplary reconstruction-based technique of blending of image data for CT cardiac applications that reduces gray scale non-uniformities in the reformatted images.

FIG. 4 is a flow chart 400 of an exemplary reconstruction-based technique of blending of image data for CT cardiac applications that reduces gray scale non-uniformities in the reformatted images.

In the exemplary embodiment, images in transition area 330 are reconstructed twice, once from each data set corresponding to gated acquisition windows 306 and 308. Averages or blends of the two reconstructions are then used to produce the final image. Blending details, including the number of blended images per transition region and the type of blending including a selectable choice of weight factors and/ or additional filtering, are used to facilitate optimization based on additional information such as scan pitch, acquisition parameters, EKG regularity, and artifact tolerance. In various embodiments of the present invention, if no redundant data is available, processing is modified to increase available data by using a larger fraction of the cardiac cycle (reduce the temporal resolution of the scan), or to skip the blending to maintain temporal resolution with an increased risk of banding artifacts.

In the exemplary embodiment, a scan data set 402 is received from first gated acquisition window 306. Corrections are selectively applied 406 to scan data set 402 and the data is view weighted 410. The view weighted data is then fan to parallel rebinned and filtered 414. The data is backprojected 418 to generate an image 422 using the data only from gated acquisition window 306. A scan data set 404 is also received from second gated acquisition window 308. Corrections are selectively applied 408 to scan data set 404 and the data is view weighted 412. The view weighted data is then fan to parallel rebinned and filtered 416. The data is backprojected 420 to generate an image 424 using the data only from gated acquisition window 308. Image 422 and image 424 are combined using blending 426 with a determined difference threshold that facilitates reducing banding, and a pixel weighting to generate a final image 428.

Figure 5:
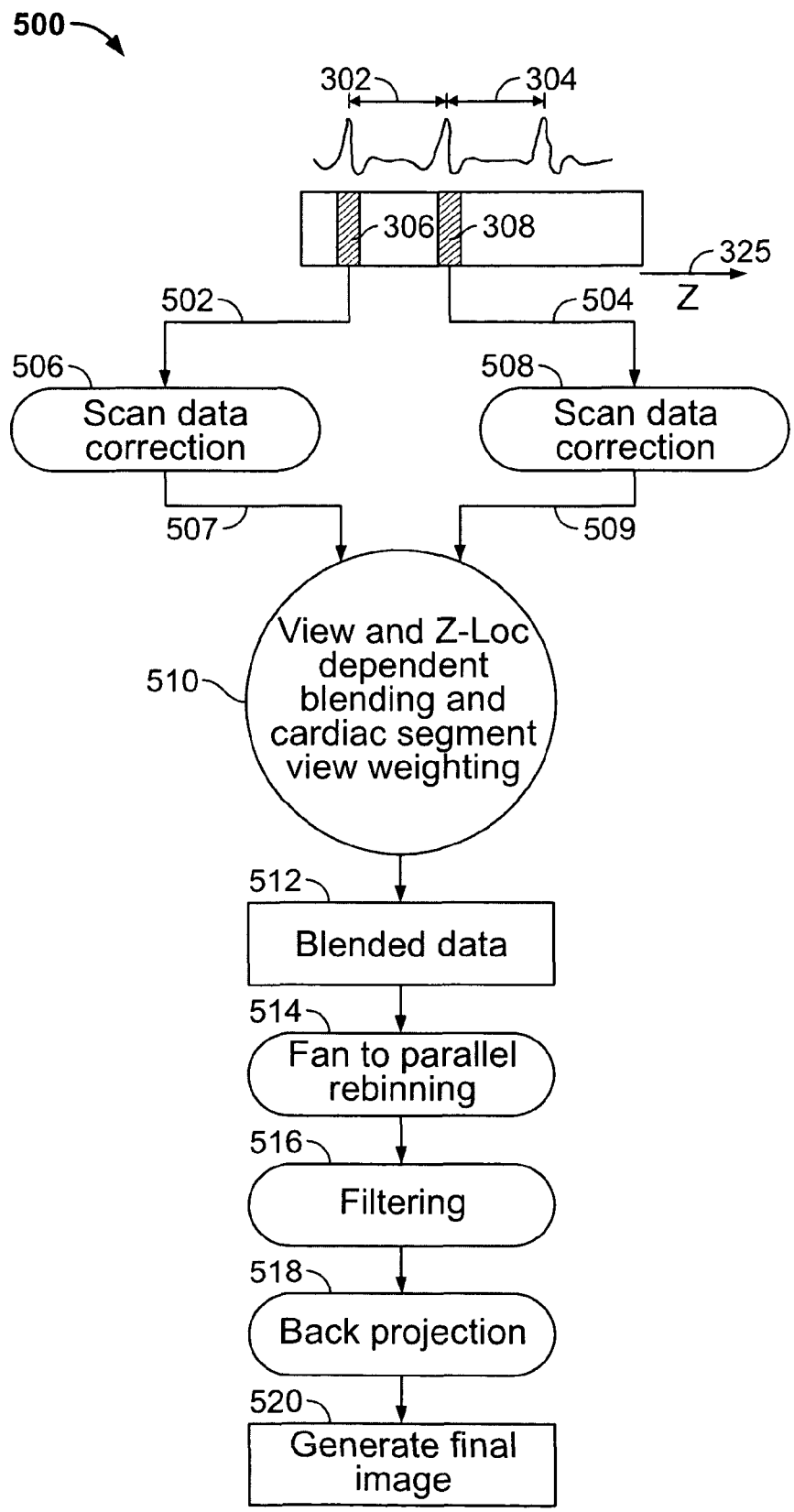
FIG. 5 is a flow chart 500 of an alternative reconstruction-based technique of blending projection data for CT cardiac applications that reduces gray scale non-uniformities in the reformatted images.

FIG. 5 is a flow chart 500 of an alternative reconstruction-based technique of blending projection data for CT cardiac applications that reduces gray scale non-uniformities in the reformatted images.

In the exemplary embodiment, a scan data set 502 is received from first gated acquisition window 306. Scan data corrections 506 are selectively applied to scan data set 502. A scan data set 504 is also received from second gated acquisition window 308. Scan data corrections 508 are selectively applied to scan data set 504. Corrected scan data 507 and 509 are combined using at least one of view and z-axis dependent blending and cardiac segment view weighting 510 to generate a set of blended projection data that is then fan to parallel rebinned 514 and filtered 516. The data is backprojected 518 to generate a final image 520.

In various embodiments of the present invention, adaptive blending is performed using weighting factors that change from pixel to pixel, depending on the difference between the multiple images reconstructed from different cardiac cycles instead of a set of pre-determined weighting functions. For example, at a particular pixel location, two of the pixel values may be approximately equal and a third pixel value may be largely different from the two. To facilitate minimizing the contribution from the third pixel, a weighting function is applied during the blending operation. In an alternative embodiment, the algorithm is implemented by weighting projection data to optimize reconstruction speed rather than implementation flexibility.

The above-described embodiments of an imaging system provide a cost-effective and reliable means for reducing banding artifacts in images. More specifically, blending image data or projection data that include redundant data for at least a portion of the images facilitates reducing the banding artifacts in the final reconstructed image. As a result, the described embodiments of the present invention facilitate imaging a patient in a cost-effective and reliable manner.

Exemplary embodiments of imaging system methods and apparatus are described above in detail. The imaging system components illustrated are not limited to the specific embodiments described herein, but rather, components of each imaging system may be utilized independently and separately from other components described herein. For example, the imaging system components described above may also be used in combination with different imaging systems. A technical effect of the various embodiments of the systems and methods described herein include at least one of facilitating imaging a patient with images wherein the banding artifacts have been substantially eliminated.

While the invention has been described in terms of various specific embodiments, those skilled in the art will recognize that the invention can be practiced with modification within the spirit and scope of the claims.

What is claimed is:

1. A computer programmed to generate computed tomographic (CT) images from scan data acquired during different biological cycles, said computer programmed to:
   receive scan data acquired during a gated acquisition window of each of a plurality of biological cycles;
   generate blended redundant projection data by combining the scan data using view dependent blending, z-axis dependent blending, and cardiac segment view weighting, wherein a segment weight is based on data acquired in an angular range at least equal to a halfscan;
   construct a first image from a first of the plurality of biological cycles;
   construct a second image from a second of the plurality of biological cycles, wherein the second image comprises a region of overlap with the first image to define a transition region; and
   construct a final image comprising the first image and the second image, wherein the transition region is defined using adaptive blending of the blended redundant projection data constructed from the first image and the second image using weighting factors that vary from pixel to pixel.

2. A computer in accordance with claim 1 further programmed to:
   receive a first plurality of images acquired during the gated acquisition window of the first of the plurality of biological cycles; and
   receive a second plurality of images acquired during the gated acquisition window of the second of the plurality of biological cycles such that the first plurality of images includes the first image and the second plurality of images includes the second image.

3. A computer in accordance with claim 1 further programmed to:
   receive first scan data acquired during a portion of a first heartbeat; and
   receive second scan data acquired during a portion of a second heartbeat.

4. A computer in accordance with claim 1 further programmed to:
   acquire first scan data during a portion of a first heartbeat; and
   acquire second scan data during a portion of a second heartbeat.

5. A computer in accordance with claim 1 further programmed to apply fan to parallel rebinning and filtering to the weighted data.

6. A computer in accordance with claim 5 further programmed to backproject the rebinned data into a generated image.

7. A computer in accordance with claim-1 further programmed to apply fan to parallel rebinning to the blended scan data.

8. A computer in accordance with claim 7 further programmed to backproject the rebinned data to generate the final image.

9. A method of reconstructing images from scan data acquired during different biological cycles, said method comprising:
receiving scan data acquired during a gated acquisition window of each of a plurality of biological cycles;
generating blended redundant projection data by combining the scan data using view dependent blending, z-axis dependent blending, and cardiac segment view weighting, wherein a segment weight is based on data acquired in an angular range at least equal to a halfscan;
constructing a first image from the first of the plurality of biological cycles;
constructing a second image from the second of the plurality of biological cycles, wherein the second image comprises a region of overlap with the first image to define a transition region; and
constructing a final image including the first image and the second image, wherein the transition region is defined comprising adaptively blending the blended redundant projection data acquired from the first image and the second image using weighting factors that vary from pixel to pixel.

10. A method in accordance with claim 9 wherein receiving scan data comprises:
receiving first image data acquired during the gated acquisition window of the first of the plurality of biological cycles; and
receiving second image data acquired during the gated acquisition window of the second of the plurality of biological cycles such that the first image data is indicative of a plurality of first images and the second image data is indicative of a plurality of second images, the plurality of first images including the first image and the plurality of second images including the second image.

11. A method in accordance with claim 9 wherein receiving scan data acquired during a gated acquisition window of each of a plurality of biological cycles comprises:
acquiring first scan data during a portion of a first heartbeat; and
acquiring second scan data during a portion of a second heartbeat.

12. A method in accordance with claim 9 further comprising applying fan to parallel rebinning and filtering to the weighted data.

13. A method in accordance with claim 12 further comprising backprojecting the rebinned data into a generated image.

14. A method in accordance with claim 9 further comprising applying fan to parallel rebinning to the blended scan data.

15. A method in accordance with claim 14 further comprising backprojecting the rebinned data to generate the final image.

16. A method of reconstructing an image of an object from scan data acquired during different biological cycles using a computed tomographic imaging system, said method comprising:
generating a first image from first scan data acquired during a first biological cycle;
generating a second image from second scan data acquired during a second biological cycle, wherein at least a portion of each of the second scan data and the first scan data is redundant scan data, and wherein the second image comprises a region of overlap with the first image to define a transition region;
generating blended redundant projection data by combining the scan data using view dependent blending, z-axis dependent blending, and cardiac segment view weighting, wherein a segment weight is based on data acquired in an angular range at least equal to a halfscan; and
constructing a final image including the first image and the second image, wherein the transition region is defined comprising adaptively blending the blended redundant projection data acquired from the first image and the second image using weighting factors that vary from pixel to pixel.

17. A computed tomographic (CT) imaging system for reconstructing an image of an object, said imaging system comprising:
a detector array;
at least one radiation source; and
a computer coupled to said detector array and said radiation source, said computer configured to:
receive scan data acquired during a gated acquisition window of each of a plurality of biological cycles;
generate blended redundant data by combining the scan data using view dependent blending, z-axis dependent blending, and cardiac segment view weighting, wherein a segment weight is based on data acquired in an angular range at least equal to a halfscan;
construct a first image from a first of the plurality of biological cycles;
construct a second image from a second of the plurality of biological cycles, wherein the second image comprises a region of overlap with the first image to define a transition region; and
construct a final image comprising the first image and the second image, wherein the transition region is defined using adaptive blending of the blended redundant projection data constructed from the first image and the second image using weighting factors that vary from pixel to pixel.

18. A computer programmed to generate computed tomographic (CT) images from scan data acquired during different biological cycles, said computer programmed to:
receive scan data acquired during a gated acquisition window of each of a plurality of biological cycles;
generate reconstructed image pixels from scan data of each of the plurality of biological cycles by combining the scan data using view dependent blending, z-axis dependent blending, and cardiac segment view weighting; and
construct a final image based on a cardiac phase and pixel values comprising adaptive blending of redundant scan data using first image data acquired during a first of the plurality of biological cycles and second image data acquired during a second of the plurality of biological cycles using weighting factors that vary from pixel to pixel, wherein the second image overlaps the first image to define a transition region.

* * * * *